United States Patent [19]

Cooper et al.

[11] Patent Number: 5,640,330
[45] Date of Patent: Jun. 17, 1997

[54] METHOD FOR ANALYZING PH TITRATION DATA

[75] Inventors: Emanuel Israel Cooper, Riverdale; David L. Rath, Stormville, both of N.Y.

[73] Assignee: IBM Corporation, Armonk, N.Y.

[21] Appl. No.: 424,778

[22] Filed: Apr. 18, 1995

[51] Int. Cl.$^6$ .................................................. G01N 31/16
[52] U.S. Cl. .................................... 364/496; 364/578
[58] Field of Search .............................. 364/496, 497, 364/498, 499, 500, 502, 578, 148

[56] References Cited

U.S. PATENT DOCUMENTS

| | | | |
|---|---|---|---|
| 3,769,178 | 10/1973 | Rothermel, Jr. . | |
| 3,875,395 | 4/1975 | Jilek . | |
| 4,266,942 | 5/1981 | Vandenbossche et al. | 364/497 X |
| 4,940,551 | 7/1990 | Riggs et al. | 364/148 X |
| 5,132,916 | 7/1992 | Gulaian et al. | 364/502 |

OTHER PUBLICATIONS

Data Reduction and Error Analysis for the Physical Sciences, by P.R. Bevington, McGraw–Hill, 1969, Chapter 11.
A Non–Linear Least–Squares Approach to the Refinement of all Parameters Involved in Acid–Base Titrations, by Giuseppe Arena, Enrico Rizzarelli, Silvio Sammartano and Carmelo Rigano, Talanta vol. 26, pp. 1–4, Pergamon Press, Ltd., 1979.
Data Analysis for Acid–Base Titration of an Unknown Solution, by William E. Gordon, American Chemical Society 1982, vol. 54, pp. 1595–1601.
Determination of Component Concentrations in Mixtures of Weak and Strong Acids and Bases by Linear Algebraic Methods, by Ari Ivaska and Istvan Nagypal, Talanta, vol. 27, pp. 721–726, Pergamon Press Ltd., 1980.
BEST—A New Program for Rigorous Calculation of Equilibrium Parameters of Complex Multi–Component Systems, by Ramunas J. Motekaitis and Arthur E. Martell, Can. J. Chem. vol. 60, 1982, pp. 2403–2409.

Program PKAS: A Novel Algorithm for the Computation of Successive Protonation Constants, by Ramunas J. Motekaitis and Arthur E. Martell, Can. J. Chem. vol. 60, 1982, pp. 168–173.
A Generalized Approach for the Calculation and Automation of Potentiometric Titrations, by J. Stur, M. Bos and W.E. VanderLinden, Analytica Chimica Acta, 158, 1984, pp. 93–111.
SUPERQUAD: An Improved General Program for Computation of Formation Constants from Potentiometric Data, by Peter Gans, Antonio Sabatini, and Alberto Vacca, J. Chem. Soc. Trans., 1985, pp. 1195–1200.
Simplex Optimization Procedure for Evaluating Equivalence Points in Sigmoidal and Segmented Titration Curves, by Domenico Perosa, Franco Magno, Gino Bontempelli and Paolo Pastore, Analytica Chimica Acta, 191, 1986, pp. 377–384.
Article entitled *pHSPECT: From pH Titration to "pH Spectroscopy"*, by Emanuel E. Cooper and David L. Rath, given at ACS Meeting in Washington, D.C. on Aug. 21, 1994.

*Primary Examiner*—Emanuel T. Voeltz
*Assistant Examiner*—M. Kemper
*Attorney, Agent, or Firm*—Barnes, Kisselle, Raisch, Choate, Whittemore & Hulbert P.C.

[57] ABSTRACT

The present invention is directed to a method that fits experimental pH titration data to a model titration curve. The model is designed to accommodate any practical number of weak acids or bases (i.e., buffers) with single or multiple $pK_a$'s in the sample and/or the titrant. It is also possible by means of the present invention to use any choice of titrant, including weak acids or bases, buffered solutions, or either an acid or base titrant for the same sample. A non-linear curve-fitting procedure is used to fit the data to the model. Volume changes, ionic strength effects, and differences between measured pH and the proton concentration function $p[H^+]$ are taken into account. Mixtures of compounds with $pK_a$'s less than 1 unit apart can be determined accurately. The results may be displayed in a deconvoluted form, facilitating the identification of compounds through their $pK_a$'s.

19 Claims, 7 Drawing Sheets

METHOD FOR ANALYZING pH TITRATION DATA

FIELD OF THE INVENTION

The present invention relates to a method for analyzing pH titration data, and more specifically to a method for curve-fitting or simulating pH titration which does not focus on titration end point and allows the quantitative determination of compounds with closely spaced acidity constants ("$K_a$'s") in mixtures.

BACKGROUND OF THE INVENTION pH titration has traditionally been one of the simplest and commonly used methods of chemical analysis. Present pH titration practice is to use automatic potentiometric titrators whenever possible because of their cost effectiveness and assistance in laboratory record keeping. Such instruments deliver a titrant at a programmed (i.e., constant or variable) rate. They measure and record the sample solution pH at short time intervals to generate tens to hundreds of data points, and calculate from the recorded data one or more titration equivalence points (henceforth "end points") from their sample concentration(s). They typically make titration less labor intensive than known manual methods and yield more objective and usually more accurate results. However, automatic potentiometric titrators typically do not make full use of the abundant data they can collect. Instead, only a few data points near a titration end point are used for calculations.

As a result, the well known problems with pH titration that have limited its usefulness still persist. For example, unless two acid or base components have acidity constants ("Ka's") that differ by about four (4) orders of magnitudes (i.e., 4 logarithmic "$pK_a$" units or more), their individual concentrations generally cannot be accurately determined by one titration. Instead, only a "total titratable acid/base" result is determinable. Also, it is difficult to analyze very weak acids or bases using known methods because the titration end point, occurring at a pH close to the pH of the titrant, is poorly defined. Similarly, the combination of medium strength acids (i.e., $pK_a \cong 2$–3.5) and strong acids cannot be accurately analyzed when in the presence of one another. The same result occurs when analyzing medium strength bases (i.e., $pK_a \cong 10.5$–12) and strong bases.

Another difficulty with known titration methods is that, to define a titration end point, a sample sometimes has to be titrated to pH values that are either acidic or basic enough to cause the degradation or precipitation of acid or base-sensitive species. Weak acid or base titrants often cannot be used because the resulting end points, which are needed when using prior art methods, will be poorly defined. Finally, even if a chemical analysis can be performed, the customary graphical representations of pH titration do not typically convey explicit information about the identity of the titrated species.

The inventors are aware of a method of calculating the titration end point, called the Gran technique, which uses more data points. Used commercially in a titration system made by Orion, the method attempts to accurately define a titration end point by an extrapolation algorithm, and can be useful in the titration of very weak acids or bases. Another titration system, made by Sanda Corporation, utilizes the experimental method of thermometric titration in an effort to determine individual concentrations when two acids or bases have dissociation constants that differ by at least 2 $pK_a$ units. Yet, even these two titration methods still focus on a titration end point, are unable to resolve the situation of closely spaced $pK_a$'s, and yield little information about the $pK_a$'s, and therefore the identities, of components in mixtures.

SUMMARY OF THE INVENTION

The present invention is directed to a system that fits experimental pH titration data to a model titration curve. The model is designed to accommodate any practical number of weak acids or bases (i.e., buffers) with single or multiple $pK_a$'s in the sample and/or the titrant. It is also possible by means of the present invention to use a wide range of titrants, including weak acids or bases, mixtures of strong and weak acids or bases, buffered solutions, or either an acid or base titrant for the same sample. A titration may be stopped far short of an end point since the end point is typically not necessary to an analysis of the titration. A nonlinear curve-fitting procedure is used to fit the data to the model. Volume changes, ionic strength effects, and differences between measured pH and the proton concentration function $p[H^+]$ are taken into account. Mixtures of compounds with $pK_a$'s less than one unit apart can be determined accurately. The results may be displayed in a deconvoluted form, facilitating the identification of compounds through their $pK_a$'s. The invention also includes the ability to simulate hypothetical titration systems without actually undertaking a titration.

In operation, the invention typically starts with data generated from an automatic potentiometric titrator, although manual or simulated titrations are also possible sources. The data is normally received in the form of $pH=pH(\delta v)$ where $\delta v$ is the volume of titrant, which is preferably added in constant increments, and pH is measured in the mixture of titrant plus sample. The pH data is inverted into a form in which titrant volume is expressed as a function of measured pH, $\delta v = \delta v(pH)$ and plotted for a preselected pH range using a preselected number of points. Interpolation and smoothing of the data are possible. Then a derivative of the volume of the titrant versus pH, $d\delta v/dpH$, is typically plotted. In a preferred embodiment, calibration techniques are available for correcting non-ideal electrode behavior and converting the pH data into hydrogen ion concentrations needed for use in the model. The calibration techniques are typically only necessary when working at low or high pH or when analyte concentrations are low. The necessary corrections are obtained in one or more separate titration runs, in which both sample and titrant compositions are accurately known, and $pK_a$'s are either far outside the range of interest (e.g., strong acids or bases), or accurately known.

There are many advantages to such an approach. The titrant volume needed to reach a given pH is easily modeled to be a function of mixture constituents. A model based on this approach is readily expandable to include any number of weak acids or weak bases (i.e., buffers) with any number of acidity constants (i.e., $pK_a$'s). The derivative of the titrant volume versus pH is closely related to the buffer capacity and to the concentrations of buffer species. When plotted, this derivative is particularly useful in designing a buffer set model for unknown sample and/or titrant solutions and in assessing the quality of the fit.

Once the data has been plotted, the buffer set and the pH data range within which the data will be fitted are selected. As noted above, a titration end point is not required. In fact, it is often preferable to exclude from the fitting pH range those data points closest to the end point, since they are the ones for which the pH measurement is least accurate and, in the absence of a calibration run, may adversely affect the quality of the fit. The buffer set comprises the number and types of "buffers" (i.e., "weak" acids and bases, each with a specified number of acidity constants, $pK_a$'s, typically between 1 and 13). Next, initial estimates, which can be rough, are preferably made for values of concentrations and $pK_a$'s. $pK_a$ estimates can be based on visible maxima and "shoulders" of the derivative plot, and for known solution components, on literature values. Before applying any curve-fitting techniques, the chosen values can be rapidly evaluated visually, using a model that relates the titrant volume to the hydrogen concentration in the mixture and the titrant to determine the resulting "goodness of fit." Finally, the pH data is then curve-fitted by a least-squares technique to accurately describe the titration.

The curve-fitting method employed is based on a nonlinear least-square fitting scheme. The method usually converges within a few iterations depending on the orthogonality of the parameters. Concurrent with the iteration, intermediate fitting curves of the form $d\delta v/dpH$ and $\delta v = \delta v(pH)$ are typically displayed to give visual feedback as to the correctness of the choice of the buffer set. A poor choice occasionally leads to convergence to an erroneous "local minimum" solution. If this occurs, the visible discrepancies between the fitted and experimental curves, especially in the derivative curve, usually make the necessary buffer-set corrections self-evident. Upon convergence, options are available to assess the goodness of fit by inspecting one of several available residual (data-model) curves and, if needed, to change the buffer set accordingly. Also available is the option to deconvolute the derivative curve into separate contributions of the sample components, including the solvent.

Simulated titration data can be generated from a buffer set and experimental parameters (e.g., a sample solution volume) to anticipate the course of a pH titration. For example, the pH obtainable when titrating a weak base with a given volume of a weak acid titrant can be calculated. The simulated data generated can be used to test predictions on the pH behavior of a given system. A further use is the evaluation of effects of operator-chosen parameters used in the program; e.g., of the small distortion caused by the data inversion operation, which is contingent on the degree of smoothing chosen at that stage.

The titration simulator is particularly valuable for educational applications in teaching the concepts of pH, weak acids/bases, buffers and buffer capacity, $pK_a$'s, and $pK_w$. Other important uses are the planning and evaluation of experiments, and testing the program's performance.

Another capability of the system is the ability to generate a buffer capacity curve from a given buffer set. This is done by using a set of equations derived from the model in the limiting case of an infinitesimal addition of a strong acid or base titrant so there is no change in the solution volume. The data derived from an actual titration by curve fitting can also be easily converted into a buffer capacity curve; the advantage is in comparing results of different titrations while eliminating the influence of titrant concentration, sample volume, and sample dilution. Applications include experiment planning and actual buffer capacity monitoring in life sciences and other areas in which buffering is paramount. Further, buffer capacity plotting provides a good educational tool for teaching the concepts of buffers and $pK_a$'s.

The pH titration model is based on the principle of mass balance that requires that the molar amounts of the hydrogen ion, hydroxide ion and buffers in the sample and titrant be conserved upon mixing. However, the volume additivity of the sample and titrant is not assumed. The mass balance equations, which assume a constant solvent concentration throughout a titration, yield an analytical expression that relates the added titrant volume to the concentrations and $pK_a$'s of the sample and titrant solutions, and to the hydrogen ion concentration of the mixture. The form of the expression lends itself to easy expansion to handle any numbers of buffers in both the titrant and/or the sample solutions, without restriction to the number of $pK_a$'s in the buffers.

BRIEF DESCRIPTION OF THE DRAWINGS

The features and inventive aspects of the present invention will become more apparent upon reading the following detailed description, claims, and drawings, of which the following is a brief description:

DETAILED DESCRIPTION OF A PREFERRED EMBODIMENT

I. Hardware

Figure 1:
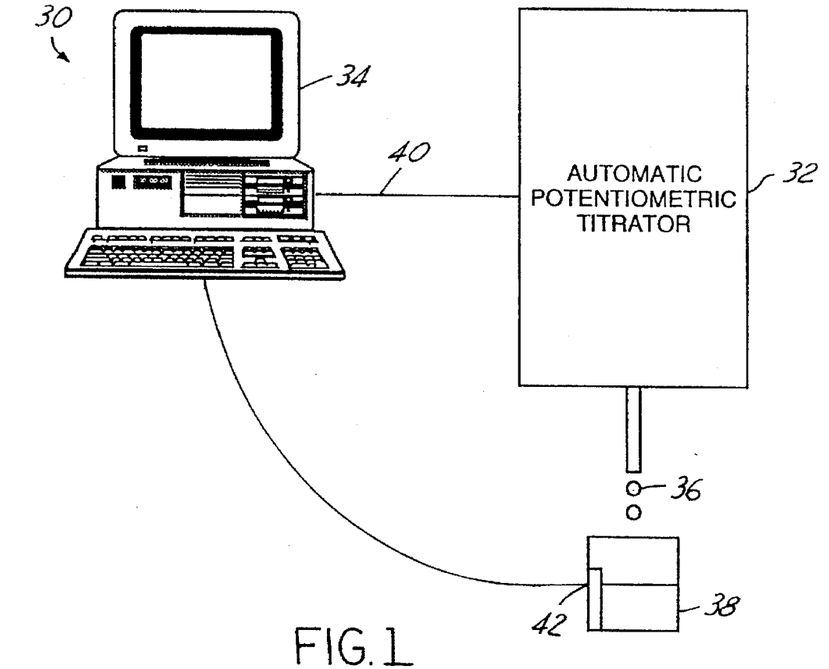
FIG. 1 is a schematic of a test system to practice the present invention.

The present invention is directed to a system 30, illustrated in FIG. 1. System 30 models experimental pH titration data and allows pH titration data to be generated from a buffer set and experimental parameters to anticipate the course of a pH titration. In a preferred embodiment, system 30 is practiced using an automatic potentiometric titrator 32 with a personal computer 34. It works with computer 34 to deliver a titrant 36 to a sample 38 at a preselected constant rate by means of line 40. Typical automatic titrators that may be used by system 30 include those made by Brinkmann, Mettler, Orion and Sanda. A PC-driven Sanda automatic titrator was used by the inventors in testing system 30.

The physical means and conditions of obtaining titration data for use with the present program are not different in principle from commonly practiced titration conditions. However, since the results are derived from a large number of data points and in order to ensure maximum accuracy, some precautions are preferably observed. In particular, the sample volume should be accurately known if accurate concentration results are needed. Further, the pH electrode reaction lag should be minimized by using a fast-reacting electrode, vigorous stirring, and a slow to moderate constant titration rate (e.g., 1–2 ml/min for 40–70 ml samples).

The ionic strength and temperature of the titration mixture should not change much during the titration, especially if accurate $pK_a$ results that can be compared to literature values are desired, and in particular if relevant data points are taken in the high basicity region (pH$\geq$10). This is easily accomplished by adding an excess of inert salt (e.g., KCl) to both the sample and titrant, and by working in a temperature-controlled jacketed flask.

Computer 34 measures and records the sample solution pH by means of a sensor such as an electrode 42. Measurements are taken at short time intervals to generate tens to thousands of data points 44 such as those illustrated in FIG. 5. A preferred electrode 42 is an Orion Ross combination pH electrode model #815600 (glass-fiber bundle junction) calibrated at two or more pH values; a single-point calibration is sufficient if a calibration titration has been run. Computer 34 comprises at least an IBM AT-type computer with 640 Kbytes of RAM, Enhanced Graphics Display, DOS 2.1; 640 Kbytes of extended memory and a math co-processor are highly desirable. Output is sent to a printer, and plots are generated using a plotter such as the IBM 7372 color plotter or equivalent.

II. Model pH titrations are performed by the pH measurement of a sample solution as known volumes of a titrant are added. The sample solution may contain any number of pH buffers (weak acids/bases) where each buffer may have multiple $pK_a$'s. For a uniprotic buffer, (e.g., acetic acid), the equation which describes the degree of protonation is $$k_1 = \frac{[HA]}{[H][A]} \quad (1)$$

with $pK_{a1} = \log_{10}(k_1)$ where $k_1$ (sometimes $k_a$) is the dissociation constant, [HA] is the concentration of the protonated portion of the buffer, [A] is that for the deprotonated portion, and [H] is the concentration of the free hydrogen ion, all in molar units. Letting $[A_T]$ be the total concentration of the buffer then $$[A_T] = [A] + [HA]. \quad (2)$$

Combining equations 1 and 2 leads to the equation $$[HA] = \frac{[H]k_1}{1 + [H]k_1} [A_T] \quad (3)$$

which will be used later in the model development. The corresponding equations for a diprotic acid are $$k_1 = \frac{[HA]}{[H][A]} \quad (4)$$

$$k_2 = \frac{[H_2A]}{[H][HA]} \quad (5)$$

which along with the definition for the total buffer concentration, $[A_T]$ $$[A_T] = [A] + [HA] + [H_2A] \quad (6)$$

yield the following relationships:

$$[HA] = \frac{[H]k_1}{1 + [H]k_1 + [H]^2 k_1 k_2} [A_T] \quad (7)$$

$$[H_2A] = \frac{[H]^2 k_1 k_2}{1 + [H]k_1 + [H]^2 k_1 k_2} [A_T]. \quad (8)$$

Similar equations for higher order protonated buffers can be easily inferred from the above development. For example, the concentration of the triprotonated form of a tetraprotic buffer is $$[H_3A] = \frac{[H]^3 k_1 k_2 k_3}{1 + [H]k_1 + [H]^2 k_1 k_2 + [H]^3 k_1 k_2 k_3 + [H]^4 k_1 k_2 k_3 k_4} [A_T]. \quad (9)$$

The solvent, usually water, can be described in a similar fashion through the equation $$k_w = \frac{[HW]}{[H][W]} \quad (10)$$

where [W] is the molar concentration of hydroxide. In this definition, the $pK_w$ for a water solvent is $$pK_w = \log_{10}\left(\frac{k_w}{[HW]}\right) \quad (11)$$

which at 25° C. has a nominal value of 14. Likewise, the concentration of water, [HW], has a nominal value of 55.4M at 25° C. The proton and hydroxide concentrations are explicitly written in anticipation of the mass balance equations discussed next. Water is formally assumed to be made entirely of protons and hydroxide ions, for accounting simplicity.

Next, equations are developed to relate the pH of a mixture with the volume of titrant added to a sample volume. The approach uses the principle of mass conservation as applied to both the hydrogen ion and the hydroxide ion, separately, which requires that the mole amounts of H$^+$ and OH$^-$, and buffers in the sample and titrant, be conserved upon mixing. However, the volume additivity of sample and titrant is not assumed.

For simplicity, consider the titration of a sample containing uniprotic buffer only and a strong acid or base titrant. For conservation of hydrogen ion, after any volume addition of titrant, $V_t$, $$V_s([H]_s + [HW]_s + [HA]_s) + V_t([H]_t + [HW]_t) = V_m([H]_m + [HW]_m + [HA]_m) \quad (12)$$

where the subscripts s, t, m refer to the quantities in the sample, titrant, and sample-plus-titrant mixture, respectively. The corresponding equation for conservation of hydroxide is $$V_s([W]_s+[HW]_s)+V_t([W]_t+[HW]_t)=V_m([W]_m+[HW]_m) \quad (13)$$

Since the total buffer mass is also conserved, $$V_s[A_T]_s=V_m[A_T]_m. \quad (14)$$

Combining equations (3) and (14), equation (12) can be written as, $$V_s\left[[H]_s+[HW]_s+[A_T]_s\left(\frac{[H]_s k_1}{1+[H]_s k_1}-\frac{[H]_m k_1}{1+[H]_m k_1}\right)\right]+ \quad (15)$$
$$+ V_t([H]_t+[HW]_t) = V_m([H]_m+[HW]_m).$$

It is not assumed that the mixture volume, $V_m$, equals the sum of the sample plus titrant volumes. Rather, the assumption is made that the mixture volume is unknown, and it is eliminated using equations (15) and (13).

We define a function $\alpha_s$ as $$\alpha_s = [A_T]\left(\frac{[H]_s k_1}{1+[H]_s k_1} - \frac{[H]_m k_1}{1+[H]_m k_1}\right) \quad (16)$$

which collects all terms that have an explicit dependence on the parameters used to describe the uniprotic buffer of the sample solution. If the sample solution contained a diprotic buffer, the function would take the form, $$\alpha_s = [A_T]\left(\frac{[H]_s k_1 + 2[H]_s^2 k_1 k_2}{1+[H]_s k_1+[H]_s^2 k_1 k_2} - \frac{[H]_m k_1 + 2[H]_m^2 k_1 k_2}{1+[H]_m k_1+[H]_m^2 k_1 k_2}\right) \quad (17)$$

using the nomenclature of equations (4) through (8). In general, the function $\alpha_s$ for a multiprotic buffer of degree, $n_\alpha$, is $$\alpha_s = [A_T]\left[\frac{\sum_{j=1}^{n_\alpha}\left(j[H]_s^j \prod_{i=1}^{j} k_i\right)}{1+\sum_{j=1}^{n_\alpha}\left([H]_s^j \prod_{i=1}^{j} k_i\right)} - \frac{\sum_{j=1}^{n_\alpha}\left(j[H]_m^j \prod_{i=1}^{j} k_i\right)}{1+\sum_{j=1}^{n_\alpha}\left([H]_m^j \prod_{i=1}^{j} k_i\right)}\right] \quad (18)$$

where $\prod_{i=1}^{j}$ denotes the product function. For a sample solution containing more than one buffer, the contribution from each buffer to the total function $\alpha_s$ is simply additive, that is, $$\alpha_s = \sum_{i=1}^{N_s} \alpha_{si} \quad (19)$$

where the sum is over the $N_s$ buffers in the sample solution and is the corresponding function for the ith buffer.

Solving equations (13) and (15) simultaneously avoids the assumption of volume additivity and its associated inaccuracy. Letting $$\delta v = \frac{V_t}{V_s} \quad (20)$$

then $$\delta v = \frac{([H]_s+[HW]_s+\alpha_s)([W]_m+[HW]_m)-([H]_m+[HW]_m)([W]_s+[HW]_s)}{([H]_m+[HW]_m)([W]_t+[HW]_t)-([H]_t+[HW]_t)([W]_m+[HW]_m)}. \quad (21)$$

Equation (21) is the basis for calculations whenever strong acids or strong bases are used as titrants.

Titrants containing buffers are incorporated into the theory in a manner similar to the development given thus far. Conceptually, the titrant is partitioned into components consisting of (a) all buffers treated as their fully protonated and undissociated entities, and of (b) an initially pH-neutral solution which receives all strong acid and strong base additions. If a buffer used to make the titrant solution is only partially protonated, then the molar amount of hydrogen ions needed for its complete protonation is reflected as an equal amount of strong base added to the initially neutral pH solution. Within this framework, the total hydrogen ion concentration of the partitioned titrant can be written as $$[H_T]_t = [H']_t + [HW]_t + \sum_{i=1}^{N_t} N_{pi}[A_T]_{ti} \quad (22)$$

where the sum is taken over all buffers in the titrant, $[A_T]_{ti}$ is the concentration of the ith buffer in the final titrant volume, $N_{pi}$ is the protonation order of the ith buffer ($N_p=2$ for a diprotic buffer), and $[H']_t$ is the hydrogen ion concentration of the unbuffered portion of the partitioned titrant. When the titrant does not contain buffers, $[H']_t$ is equal to $[H]_t$ of equation (12).

Similarly, the total hydroxide ion concentration of the partitioned titrant can be written as $$[W_T]_t = [W']_t + [HW]_t \quad (23)$$

with $[W']_t$ as the hydroxide ion concentration of the unbuffered portion of the partitioned titrant. As before, when the titrant does not contain buffers, $[W']_t$ is equal to $[W]_t$ of equation (13). The concentrations, $[H']_t$ and $[W']_t$, are related through the solvent dissociation equations, (10) and (11). The concentrations are determined from the net amount of acid and base added to the partitioned titrant. The net amount of acid, $[H_{NET}]_t$, is set equal to the concentration of any added strong acid with respect to the final volume of the titrant. Likewise, the net amount of base, $[W_{NET}]_t$, is set equal to the concentration of any added base plus the sum of concentrations corresponding to the amount of hydrogen ions needed to fully protonate each buffer in the titrant. The relationship describing these quantities to that of the unbuffered portion of the partitioned titrant is $$[H']_t - [W']_t = [H_{NET}]_t - [W_{NET}]_t \quad (24)$$

where only $[H']_t$ and $[W']_t$ are related through the solvent dissociation equations, (10) and (11). When the value of the right-hand side of equation (24) is positive, that is, when a greater amount of acid is added than base, then along with equation (10) the hydrogen ion concentration of the partitioned titrant can be evaluated from $$[H']_t = \frac{[H_{NET}]_t - [W_{NET}]_t}{2} + \quad (25)$$

-continued $$\sqrt{\left(\frac{[H_{NET}]_t - [W_{NET}]_t}{2}\right)^2 + \frac{[HW]_t}{k_w}}$$

from which the evaluation of $[W']_t$ follows from equation (10). Similarly, when the value of the right-hand side of equation (24) is negative or zero, then $[W']_t$ is evaluated from $$[W']_t = \frac{[W_{NET}]_t - [H_{NET}]_t}{2} + \sqrt{\left(\frac{[W_{NET}] - [H_{NET}]}{2}\right)^2 + \frac{[HW]_t}{k_w}} \quad (26)$$

and $[H']_t$ by equation (10).

Thus, equation (15) for the conservation of mass for the hydrogen ion can be written as, $$V_s([H]_s + [HW]_s + \alpha_s) + V_t\left([H']_t + [HW]_t + \sum_{i=1}^{N} N_{pi}[A_T]_{ti}\right) = \quad (27)$$

$$V_m\left([H]_m + [HW]_m + \sum_{i=1}^{N_t}\left(\sum_{j=1}^{N_{pi}} j[H_jA]_{ti}\right)\right)$$

where the definition of the function $\alpha_s$ is used. See, equations (16) and (19). In this equation, the double summation in the mixture volume term reflects the total hydrogen ion concentration tied to the partially protonated buffers of the titrant additions. The mass of each titrant buffer is also conserved upon mixing, and for the ith titrant buffer, gives the relation $$V_t[A_T]_{ti} = V_m[A_T]_{mi} \quad (28)$$

Rearranging equation (27) by collecting all terms involving the titrant buffer into a new function, $\beta_t$, gives $$V_s([H]_s + [HW]_s + \alpha_s) + V_t([H']_t + [HW]_t + \beta_t) = V_m([H]_m + [HW]_m) \quad (29)$$

For a single uniprotic buffer in the titrant, the function $\beta_t$ is $$\beta_t = [A_T]_t\left(1 - \frac{[H]_m k_1}{1 + [H]_m k_1}\right) \quad (30)$$

and for a single diprotic buffer in the titrant, the function $\beta_t$ is $$\beta_t = [A_T]_t\left(2 - \frac{[H]_m k_1 + 2[H]_m^2 k_1 k_2}{1 + [H]_m k_1 + [H]_m^2 k_1 k_2}\right). \quad (31)$$

In general, the function $\beta_t$ for a multiprotic buffer of degree, $n_\beta$, is $$\beta_t = [A_T]_t\left[n_\beta - \frac{\sum_{j=1}^{n_\beta}\left(j[H]_m^j \prod_{i=1}^{j} k_i\right)}{1 + \sum_{j=1}^{n_\beta}\left([H]_m^j \prod_{i=1}^{j} k_i\right)}\right] \quad (32)$$

where $\Pi_{i=1}^{j}$ denotes the product function. For several buffers in the titrant, the contribution from each buffer to the total function $\beta_t$ is simply additive, that is $$\beta_t = \sum_{i=1}^{N} \beta_{ti} \quad (33)$$

where the sum is over the N buffers in the titrant and is the corresponding function for the ith buffer.

The relation describing the conservation of hydroxide ion is identical to equation (13) with the substitution of W for W, as previously discussed. Thus, combining these equations leads to the more general relation $$\delta v = \frac{([H]_s + [HW]_s + \alpha_s)([W]_m + [HW]_m) -}{([H]_m + [HW]_m)([W]_s + [HW]_s)} \quad (34)$$
$$\frac{([H]_m + [HW]_m)([W']_t + [HW]_t) -}{([H']_t + [HW]_t + \beta_t)([W]_m + [HW]_m)}$$

where $\delta v$ is defined by equation (20). Therefore, equation (34) expresses the functional relationship of the titrant volume with the buffer concentrations and $pK_a$'s without any restriction on the number or types of buffers in either the sample or titrant solutions. Furthermore, equation (34) places no restrictions on the solvent used in either the titrant or the sample solution.

The model's usefulness depends on its expressions being determined by easily measurable quantities, specifically $[H]_m$. Over much of the pH range, and under a range of common working conditions, experimentally measured pH can be assumed to be equal to $-\log[H]_m$. This, however, is only an approximation and breaks down at low or high pH values. An important feature of the invention is the availability of a "dynamic pH calibration" procedure, whereby pH readings obtained during a titration of a strong acid with a strong base (or vice versa) are compared to the values of mixture solution "concentration pH" or "$pH_c$", based on calculated hydrogen concentration:

$$pH_c = -\log_{10}([H]_m) \quad (35)$$

where $[H]_m$ represents the concentration of the free hydrogen ion for the sample-plus-titrant mixture. $[H]_m$ is the essential experimental variable for curve-fitting calculations. The purpose of the dynamic calibration is twofold: (a) to extend the pH range available for accurate curve-fitting and $pK_a$ measurement to below pH~3 and above pH~10.5, where pH and $pH_c$ gradually diverge from each other in a non-linear fashion; and (b) to correct for inaccuracies in pH reading under actual, continuous titration (i.e., dynamic conditions), rather than through a lengthy and, for our purpose, less relevant process of point-by-point calibration. In the latter there are consecutive steps of titrant addition, waiting for equilibration, and reading pH, as discussed in the literature (e.g., A. Avdeef, J. E. A. Comer and S. J. Thomson, *Anal. Chem.* 65, 42 (1993), incorporated herein by reference). Besides the intrinsic difference between pH reading and $pH_c$, the dynamic calibration can largely correct for the effects of many other sources of inaccuracies, including non-ideal pH-versus-voltage electrode slope, inaccurate temperature measurement or compensation, inaccurate assessment of $pK_w$, time constants associated with electrode response, or stirring efficiency. It is possible to obtain highly accurate curve-fitting and $pK_a$ results while using just a one-point pH calibration of the electrode and no temperature compensation of the pH readings, provided that a dynamic calibration is run under the same conditions (including temperature) as the sample titration.

The calibration procedure entails the pH titration of an accurately known amount of strong acid with a strong base of accurately known concentration (or vice versa), under titration conditions as close as possible to those to be used for the sample(s). For each experimental pH data point, a $pH_c$ value is calculated from known experimental parameters. Then, using the Marquardt method discussed in Marquardt, D. W., J. Soc. Indust. Appl. Math. 11(2), 432 (1963), incorporated herein by reference, the $pH_c$ values are curve-fitted to the equation $$pH_c = S_A pH + a_0 + a_1[H] + a_2[H]^2. \tag{36}$$

Here $S_A$, $a_0$, $a_1$ and $a_2$ are the parameters to fit, and pH and [H] are the measured (data) quantities with $pH = -\log_{10}[H]$ and, similarly for the basic pH region, $$pH_c = S_B pH + b_0 + b_1[W] + b_2[W]^2 \tag{37}$$

where $pH_c = pK_w + \log_{10}[W]$ with [W] being the molar concentration of hydroxide, which is intrinsically dependent on the $pK_w$ of the solvent (which varies with temperature and ionic strength). Since the data are obtained in a dynamic regime, the optimized parameters obtained for a given set of conditions in a titration of an acid sample with a base titrant are usually slightly different from those obtained under the same conditions and for the same pH range when a base sample is titrated with an acid titrant.

An option is also provided to generate partial calibration files for the acidic region and the basic region and to pair them into a usable whole-range calibration file. Thus, effects from large variations in ionic strength throughout the calibration range can be avoided.

The calculation of buffer capacity, is closely related to the titration equations discussed above, but affords a simpler mathematical treatment. The buffer capacity quantifies the ability of a solution to withstand changes in its pH when strong acids or bases are added to it. For the case of adding a strong acid to the sample solution under investigation, and within the nomenclature previously established, the buffer capacity $C_b$ can be defined through the relationship $$C_b = \lim_{V_r \to 0} \left[ \frac{d}{dpH_m} \left( \frac{[H]_t V_t}{V_s} \right) \right]. \tag{38}$$

Equation (38) describes an intrinsic property of the sample, which can be shown to be independent of titrant concentration. Therefore, the titrant may be assumed to be anhydrous; consequently, for the case of adding a strong acid to the sample solution under investigation, the conservation-of-mass expressions for the proton and hydroxide ion concentrations are, respectively, $$V_s([H]_s + [HW]_s + \alpha_s) + V_t[H]_t = V_m([H]_m + [HW]_m) \tag{39}$$

and $$V_s([W]_s + [HW]_s) = V_m([W]_m + [HW]_m) \tag{40}$$

where $\alpha_s$ is defined as in equations (16–19). Moreover, anticipating the limiting case of an infinitesimal addition of titrant, the assumption of volume additivity, $$V_s + V_t = V_m \tag{41}$$

is rigorously correct. Subtraction of equation. (40) from (39), along with use of the volume additivity assumption, leads to the expression $$\frac{[H]_t V_t}{V_s} = \tag{42}$$

-continued
$$\left( \frac{[H]_m - [W]_m}{V_s} \right) V_t + ([H]_m - [W]_m - [H]_s + [W]_s - \alpha_s)$$

Noting that $$\frac{d}{dpH_m} = -[H]_m \log_{10} \frac{d}{d[H]_m} \tag{43}$$

and that, by definition from equation (10), $$\frac{d[W]_m}{d[H]_m} = -\frac{[W]_m}{[H]_m}, \tag{44}$$

the buffer capacity expression acquires the form $$C_b = \log_{10} \left( [H]_s + [W]_s + [H]_s \lim_{V_r \to 0} \left( \frac{-d\alpha_s}{d[H]_m} \right) \right) \tag{45}$$

where the term containing $\alpha_s$ is evaluated for the specific composition of the sample solution. If, for example, the latter contains only one uniprotic buffer, then the buffer capacity is described by the relation $$C_b = \log_{10} \left[ [H]_s + [W]_s + \frac{[A_T] k_1 [H]_s}{(1 + [H]_s k_1)^2} \right] \tag{46}$$

A similar evaluation of the buffer capacity by instead considering a strong base titrant results in equations identical to (44) and (45).

III. Implementation

Figure 2:
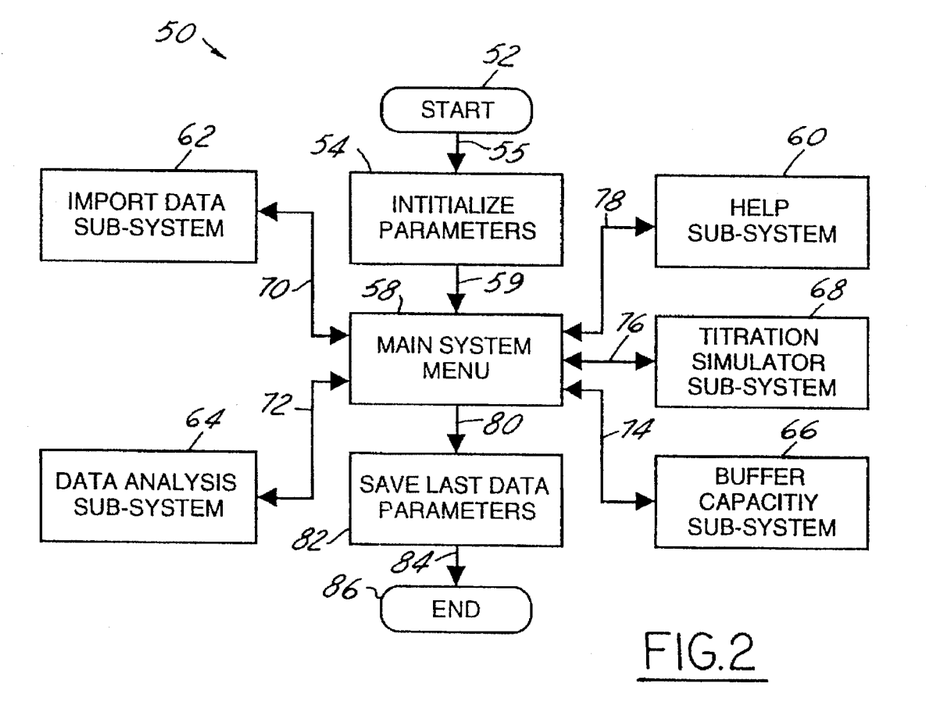
FIG. 2 is a program schematic providing an overview of an embodiment of the present invention.

FIG. 2 illustrates a program schematic 50 providing an overview of one embodiment of the present invention. Using computer 34, a program is entered at start point 52. Parameter initialization takes place at location 54, connected to start point 52 by line 55. Directories where data files may exist are read in, program options are set, and last data parameters are preferably used. If there are no data parameters, a dummy buffer template is set. The program then passes to a main system menu 58 as shown by line 59. From menu 58, a help sub-system 60, an import data sub-system 62, a data analysis sub-system 64, a buffer capacity sub-system 66, or titration simulator sub-system 68 may be selectively accessed as shown by two-way lines 70, 72, 74, 76, and 78, respectively. When the program is to end, main system menu 58 is left as shown by line 80. The last data parameters are saved at location 82. The program terminates at end point 86, which is connected to location 82 by line 84.

Figure 3:
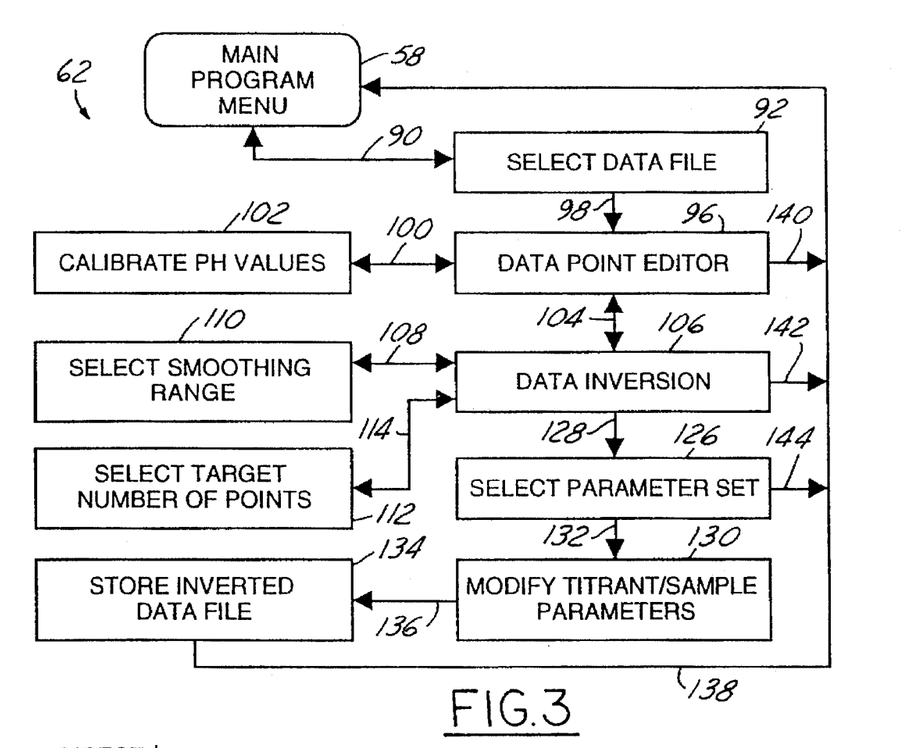
FIG. 3 is a more detailed schematic of an import data sub-system illustrated in FIG. 2.
Figure 4:
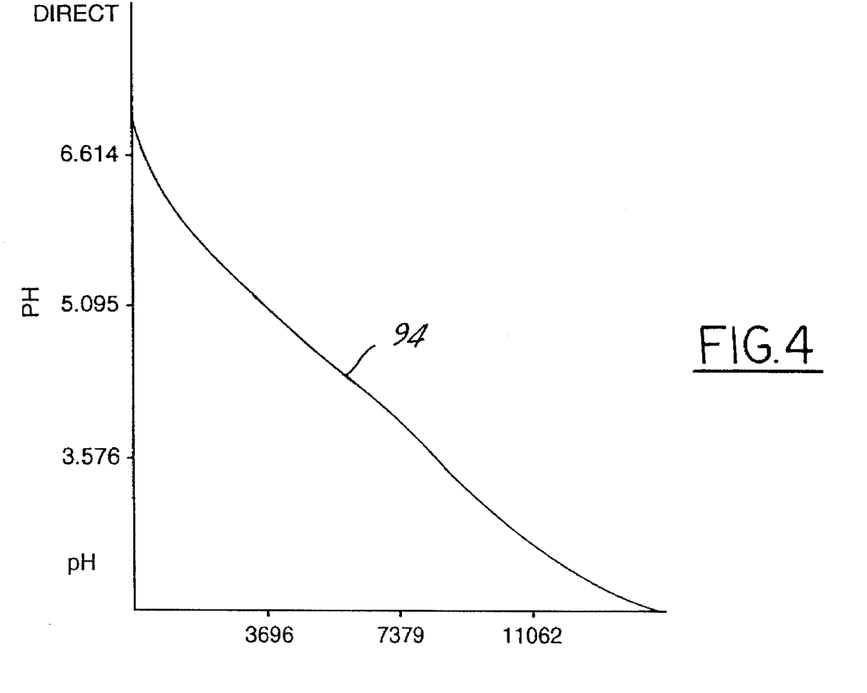
FIG. 4 is a typical prior art titration curve using an automatic titrator involving acid titration of a very weak multi functional base.

While any of the sub-systems may be accessed from menu 58 at any time or the program ended, typically import data sub-system 62 is accessed first from menu 58. A schematic of import data sub-system 62 is illustrated in FIG. 3. A data file is selected at location 92, which is tied to the main program menu by two-way line 90. Typically, the data file starts with data generated from titrator 32 although manual titration data or simulated titration data can also be used. The data is normally in a tabular form with columns representing pH and $\delta v$, where $pH = pH(\delta v)$ and $\delta v$ is the cumulative volume of titrant. FIG. 4 shows a typical titration curve 94 for titration of trisodium citrate, a very weak multi functional base, with HCl 0.2M. At the time that curve 94 was generated, the ionic strength ("I") was 0.1, temperature ("T") was 23° C., the volume of the sample ("$V_s$") was 60.1 mL, and the pH range to be fitted by system 30 was 2.06 to 6.99. FIG. 4, which represents the same set of data in the traditional way, was generated by the program associated with titrator 32 and is not part of the present invention. Note in particular the absence of an end point.

Figure 5:
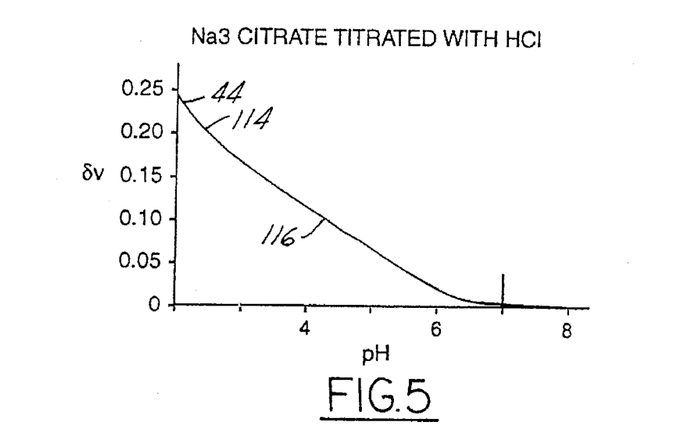
FIG. 5 is a plot of titration volume with respect to pH for the experimental data of FIG. 4 and the model of the present invention.

Once data such as that graphically represented in FIG. 5 is inputted at location 92 of FIG. 3, data point editing may take place at location 96 using a data point editor. Line 98 shows the interrelationship between locations 92 and 96. Data editing is typically only undertaken with actual raw data, to remove obviously spurious points inadvertently generated by titrator 32, or to remove data points 44, shown in FIG. 5, that are not needed to model the pH titration.

The data may also undergo pH calibration at location 102, as shown by line 100. Before using system 30 with unknown test data, the readings of electrode 42 are preferably "dynamically calibrated" using real titrations wherein the expected pH is known, in the manner discussed above. A comparison is made between the readings provided by electrode 42 and associated measurement instruments, and the value based on expected hydrogen ion concentration [H]. A correction curve is then generated. Typically, a number of titrations are used for different titration conditions (e.g., pH range—acidic or basic, electrode, temperature, or ionic strength), with each titration and correction curve stored in a segment file as part of the data analysis sub-system 64 discussed further below. At location 102 the appropriate segment files are joined together to create a "pH calibration" curve. Because the $pK_w$ of the solvent may vary, it is also inputted at location 102. If no change is made, the solvent is assumed to be water and a default $pK_w$ of 14 is used.

Once any calibration is undertaken at location 102 or editing at location 96, the program passes to undertake data inversion at location 106, as shown by line 104. Alternatively, data editing or pH calibration may be undertaken when at location 106 as shown by the bi-directional nature of lines 104 and 100. The smoothing range for evaluating the inverted derivative $d\delta v/dpH$ may be selected at location 110, connected to location 106 by two-way line 108. Preferably, an interval of 2n+1 data points ($2 \leq n \leq 9$) centered around each experimental data point is used for smoothing, by fitting to a traveling quadratic to compensate for the granularity of the data, in accordance to the method described by A. Savitsky and M. J. E. Golay (Anal. Chem. 38, p. 1627 (1964); incorporated by reference). A target number of inverted data points is selected at location 112 as shown by two-way line 114. When this target number is different from the number of experimental data points retained at location 96, the smoothing range selected at location 110 is used to interpolate as needed. The selection of the target number of inverted data points allows a better match of the necessary extent of the curve-fitting calculations to time constraints and hardware capabilities. The data inversion is then performed at location 106, generating a replacement set of inverted data points. For example, 700 experimental data points may be interpolated and inverted to provide a set of 200 inverted points.

As shown in FIG. 5, the pH data plotted in FIG. 4 is inverted into a form at location 106 wherein titrant volume is expressed as a function of measured pH, $\delta v = \delta v(pH)$ and plotted for a preselected pH range using a preselected number of points 44. Curve 114, the broken line, is a plot of the experimental data, and curve 116, the continuous line, is a plot using the model described above. The model very closely follows the actual data. The Y-axis represents $\delta v$ as defined in equation (34) and the X-axis represents pH. Inversion is undertaken because the titrant volume for a given pH is easily modeled to be a function of mixture constituents and is readily expandable to include any number of weak acids or weak bases (i.e., buffers) with any number of acidity constants (i.e., $pK_a$'s).

Figure 6:
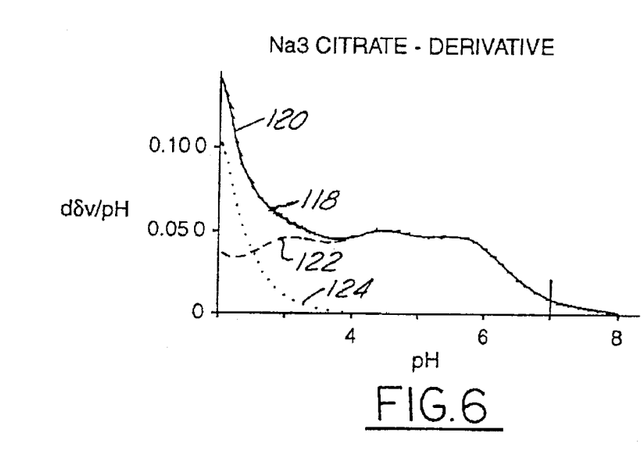
FIG. 6 is a plot of the derivative of titration volume with respect to pH for the experimental data of FIG. 4, the model, and the deconvolution of the mixture into components.
Figure 15:
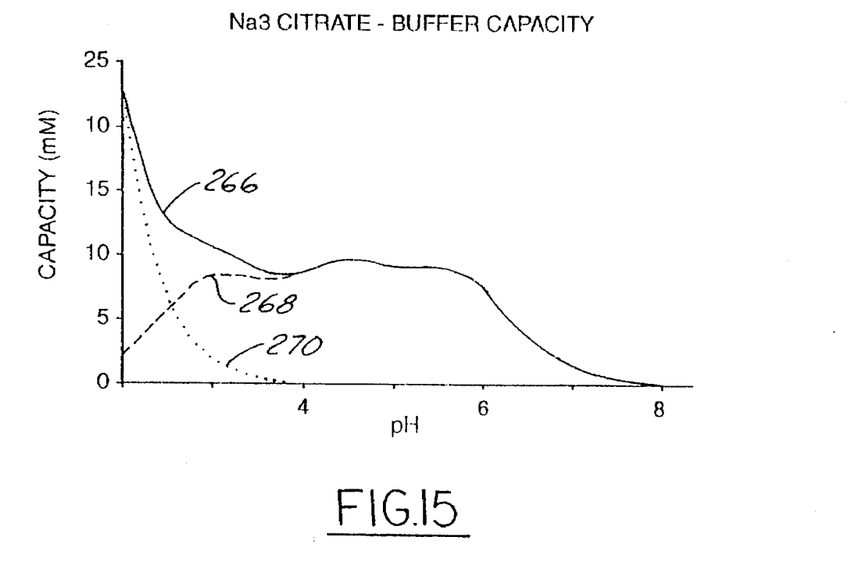
FIG. 15 is a plot of buffer capacity derived from the titration data of FIG. 4.

Then a derivative of the volume of the titrant versus pH ($d\delta v/dpH$) is typically plotted as shown in FIG. 6. The derivative of the titrant volume versus pH is closely related to the buffer capacity (which it approaches, as illustrated in FIG. 15, as the titrant volume added approaches zero,) and to the concentrations of buffer species. When plotted, it is particularly useful in designing a buffer set model for unknown sample solutions and in assessing the quality of the fit. In FIG. 6, the data is shown by broken curve 118, the model curve is shown by curve 120, and deconvolution into components' contributions is shown by broken curve 122 (citric acid) and by dotted curve 124 (the solvent).

Figure 7:
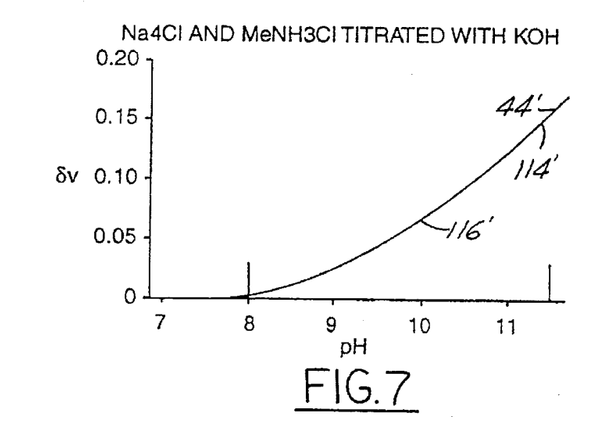
FIG. 7 is a plot of titration volume with respect to pH for base titration of a mixture of weak acids according to the model.
Figure 8:
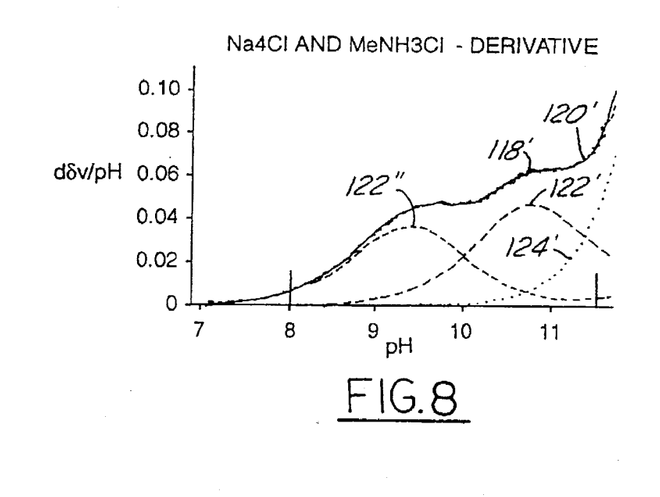
FIG. 8 is a plot of the derivative of titration volume with respect to pH for the data of FIG. 7, the model, and the deconvolution of the mixture into components.

FIG. 7 plots titrant volume as a function of measured pH, $\delta v = \delta v(pH)$ and FIG. 8 plots a derivative of titrant volume versus pH, $(d\delta v/dpH)$, for a base titration of a mixture of two very weak acids. The plots represent the titration of a mixture of ammonium chloride ($NH_4Cl$) and methylamine hydrochloride ($MeNH_3Cl$) with KOH 0.2M. The ionic strength ("I") was 0.055, temperature ("T") was 25° C., the volume of the sample ("$V_s$") was 40 ml, and the pH range to be fitted was 8.00–11.50. FIG. 7 has a curve 114' of experimental data represented by data points 44' and a curve 116' calculated using the model. In FIG. 8, the data is shown by broken curve 118', the model results are shown by curve 120', and deconvolution into component contributions is shown by broken curves 122', 122", and 124', representing the $NH_4CL$, $MeNH_3CL$, and medium, respectively.

Once the data has been inverted at location 106 of FIG. 3 and optionally plotted, a parameter set is selected at location 126 as shown by line 128. A default resident set of parameters may be used. Alternatively, a pre-saved buffer template may be recalled, as discussed further below. Once the parameter set is chosen at location 126, it is possible to modify titrant and sample parameters at location 130, accessed by means of line 132. These parameters include type (strong/weak) and concentrations of acids/bases in titrant, $pK_w$ and solvent concentration, volume of sample, and the name of the output file and any comments associated with the named file.

A special menu is available at location 130 for the treatment of $pK_w$. The preferred option is to calculate $pK_w$ as a function of temperature, sample ionic strength, and the identity of the common salt used to stabilize the latter. Calculation is performed by means of a multi-parameter equation, which is the preferred implementation, contains 11 salt-specific parameters. This is an extension of equations (15-2-3)–(15-2-7) used by H. S. Harned and B. B. Owen in *The Physical Chemistry of Electrolyte Solutions*, Third edition, Reinhold, N.Y. 1958, incorporated herein by reference. The individual set of parameter values for each salt is derived by non-linear curve-fitting of tabulated literature data on $pK_w$ dependence on temperature and ionic strength (mostly from Harned & Owen, loc cit) and on molarity to molality conversion. As an alternative to calculation, an estimated value can also be entered; or else, $pK_w$ can be given the status of a variable, to be optimized in the subsequent curve-fitting process.

The inverted data is stored at location 134 with location 134 interconnected with location 130 by line 136. Then, as illustrated by line 138, control is passed back to the main system menu 58. Control may also be passed back to menu 58 at locations 96, 106, or 126, as shown by lines 140, 142, and 144, respectively.

Figure 9:
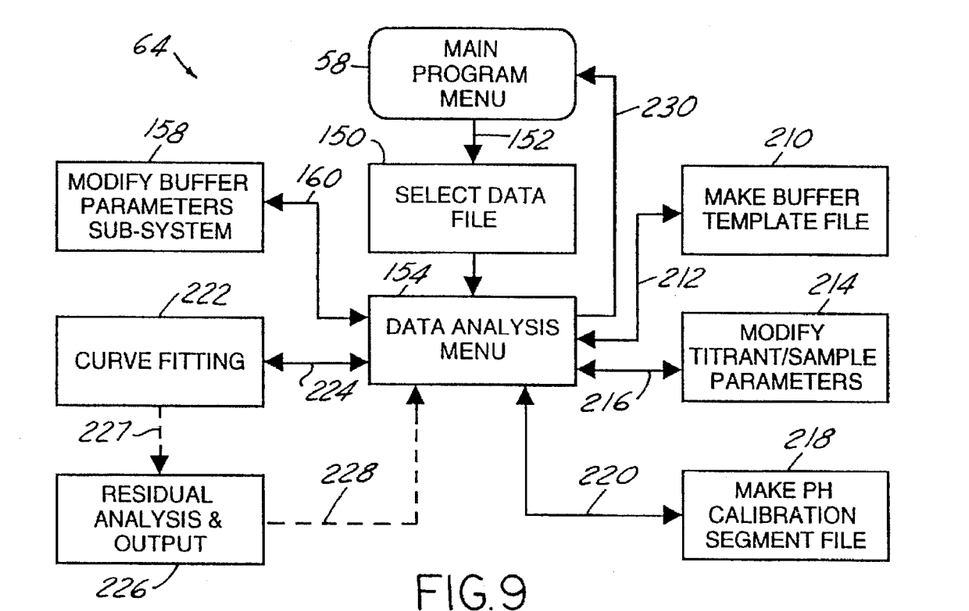
FIG. 9 is a more detailed schematic of a data analysis sub-system, illustrated in FIG. 2.

After the necessary data has been imported, data analysis sub-system 64 is typically accessed next, and a schematic of the sub-system is shown in FIG. 9. A data file is first selected at location 150, as shown by line 152. Sub-system 64 uses either an inverted pH data file generated by sub-system 62 or a simulated pH data file generated by sub-system 68. Then a data analysis menu 154 is available as shown by line 156.

Figure 10:
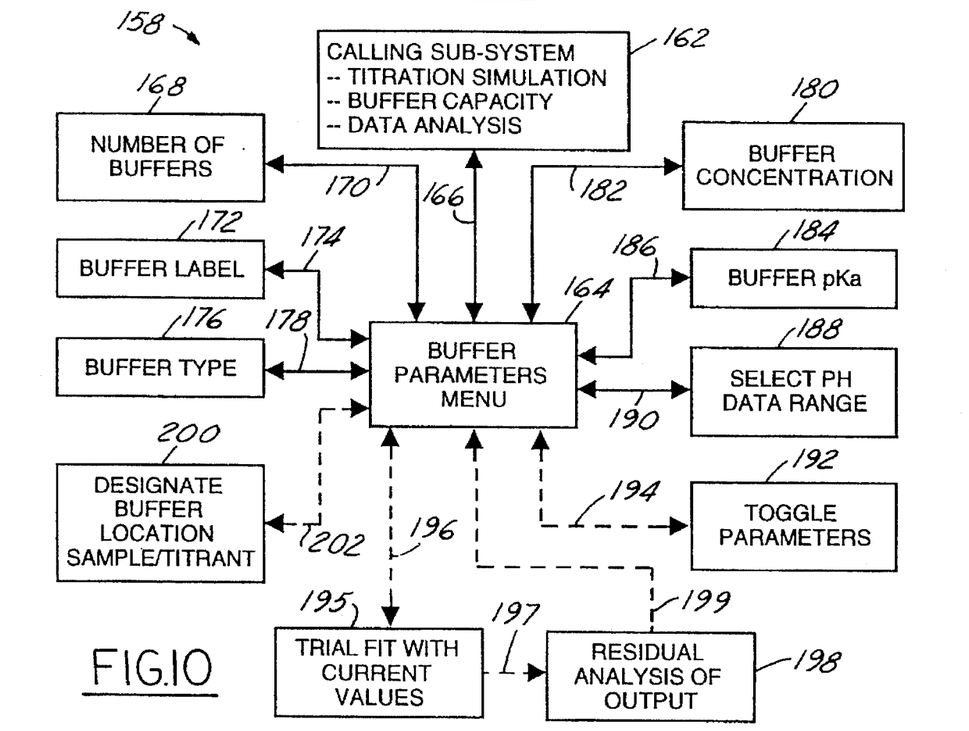
FIG. 10 is a more detailed schematic of a "modify buffer parameters" sub-system, illustrated in FIG. 2.

A modify buffers parameters sub-system 158, illustrated in the schematic of FIG. 10, is selectively available as shown by two-way line 160. As noted at location 162 of FIG. 10, sub-system 158 may be called by data analysis sub-system 64, buffer capacity sub-system 66 or titration simulator 68. Once sub-system 158 is called, however, control is passed to buffer parameter menu 164 as shown by two-way line 166. Line 166 also illustrates that control is returned to the calling sub-system when sub-system 158 is no longer needed.

From buffer parameter menu 164, a series of entries are made to create the buffer parameters required by the model described above. Buffers are added to, or removed from the resident buffer set at location 168 as shown by two-way line 170. A starting buffer set for analysis of an unknown sample preferably contains one uniprotic buffer for each visible peak or shoulder in the inverted derivative (i.e., curve 118 in FIG. 6). If prior knowledge exists on other buffers being present, they too are included in the set. Then buffer labels may be given at location 172, two-way line 174 connecting location 172 with menu 164. Even when dealing with unknown compounds, a buffer label is useful. A "buffer type", indicating the number of dissociable protons in the maximally protonated molecule, is entered at location 176, as shown by two-way line 178. The default option is one proton per buffer. Initial estimates, which can be rough, are made for each buffer concentration at location 180 as shown by two-way line 182, and buffer $pK_a$ at location 184 as shown by two-way line 186. $pK_a$ estimates can be based on the position of the maxima or shoulders on a derivative plot such as plot 118 of FIG. 6, and for known solution components, on literature values. The pH data fitting range is selected at location 188 as shown by two-way line 190. As discussed above, titration end points are typically not required by system 30. By choosing only the necessary pH range for curve fitting, as discussed further below, curve fitting will be faster and sometimes more accurate.

Several additional options are available if buffer parameters sub-system 158 is called by the data analysis sub-system 64. To aid in curve-fitting by reducing the number of variables, it is possible to toggle parameters as either a variable or a constant from menu 164 at location 192 as illustrated by two-way dashed line 194. Safeguards are present to avoid turning the last variable into a constant. In a preferred embodiment of the invention, there are typically no more than approximately nine (9) variables at one time. Then, before applying any curve fitting techniques, the chosen values can be visually evaluated, if desired, using the model at location 195 using two-way dashed line 196, to determine the resulting "goodness of fit".

If desired, options are available at location 198, by means of line 197, to analyze the resulting fitted curve for systematic errors (as opposed to random noise). This is done by inspection of the curve of residuals, $$\left[\frac{d\delta v}{dpH}\right]_{data} - \left[\frac{d\delta v}{dpH}\right]_{model} \quad (47)$$

either in its initial form or after optional smoothing. Optionally, the residuals curve of δv or its integral can be plotted and inspected instead. The shape of the curve of residuals can help decide whether the buffer set needs changes, e.g., whether the addition of a buffer to the set is likely to improve the quality of the fit, and what the initial $pK_a$ value of the additional buffer should be.

Figure 11:
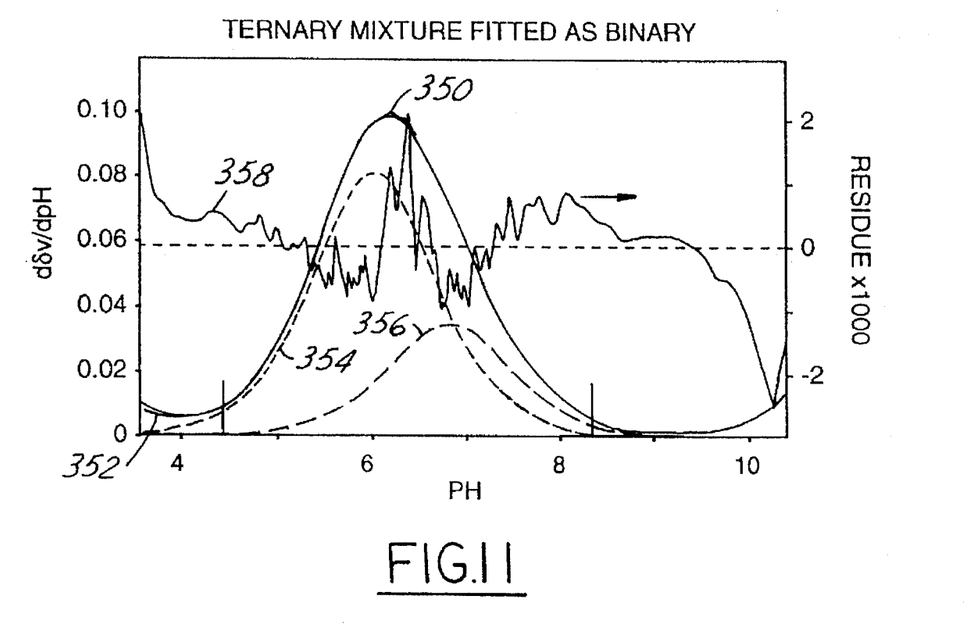
FIG. 11 is a plot of the derivative of titration volume with respect to pH for experimental data, the model (curve fitting done assuming two buffers), and the deconvolution of the mixture into components with a superimposed curve of derivative residuals.
Figure 12:
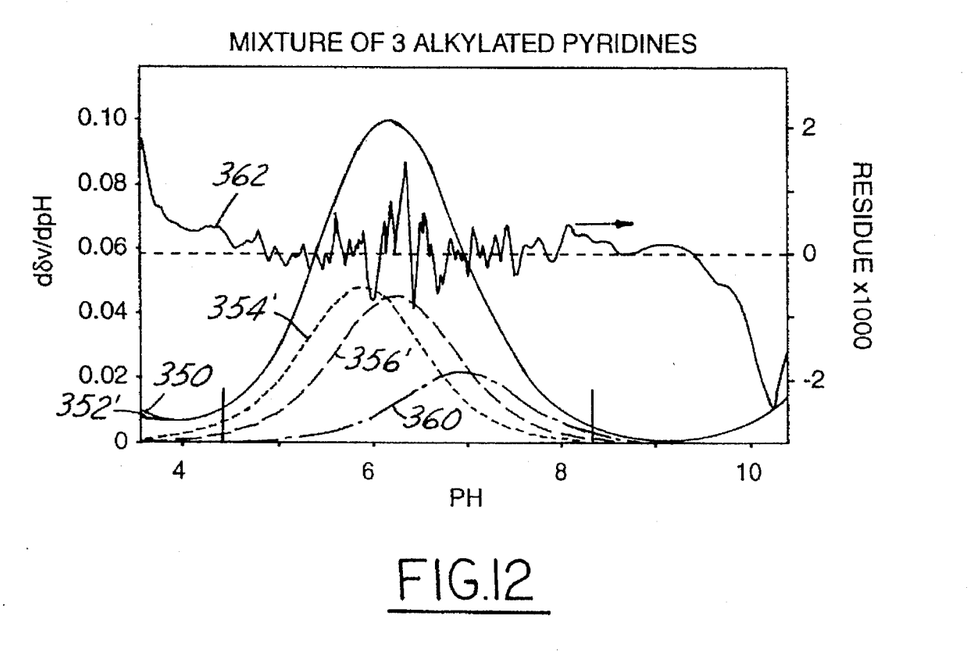
FIG. 12 is similar to FIG. 11 and based on the same data, but curve-fitting was done assuming three buffers.

Residual curves are illustrated in FIGS. 11 and 12 for a base titration (KOH 0.1M) of a three-component sample of hydrochlorides of hard to separate substituted pyridines with closely spaced $pK_a$s. As with FIGS. 6 and 8, the Y-axis represents a derivative of titrant volume (dδv/dpH) and the X-axis represents pH. The first component is 3-picoline with a $pK_a$ of 5.898 and a boiling point of 144° C., the second component is 4-picoline with a $Pk_a$ of 6.244 and a boiling point of 144° C., and the third component is 2,6-lutidine with a $pK_a$ of 6.964 and a boiling point of 144° C. In FIG. 11 the plotted data is shown by curve 350. The calculated model, based on curve fitting done by assuming only two buffers, is shown by curve 352 and deconvoluted into component contributions as shown by broken curves 354 (3-picoline) and 356 (4-picoline). A curve 358 of derivative residuals is then superimposed. The shape of curve 358 suggests that the buffer set needs changes. In FIG. 12, curve 350 is again plotted. The calculated model, based on curve fitting done by assuming three buffers, is shown by curve 352' and deconvoluted into component contributions as shown by broken curves 354' (3-picoline), 356' (4-picoline), and 360 (2,6-lutidine). A curve 362 of derivative residuals is then superimposed. Curve 362, when compared to curve 358, correctly suggests that the assumption of a three buffer set is better than an assumption of a two buffer set. In addition, a Fourier transform of the residuals curve can be calculated and displayed. This is particularly useful in revealing periodic noise stemming from experimental parameters (e.g., titrant injection rate, stirring rate, or data collection frequency), and from resonances among such parameters).

As illustrated in FIG. 10, control is returned to Buffer Parameters Menu 164 by means of line 199. Then additional changes to the buffer parameter set may be made if required before undertaking curve-fitting. This procedure is a valuable time-saver in cases with a large number of variables.

Finally, it is possible to optionally designate the buffer location for either sample 38 or titrant 36 at location 200, as shown by two-way dashed line 202 at location 200, if the modify buffer parameters sub-system 158 is called by either the data analysis sub-system 64 or the titration simulator sub-system 68. By enabling the toggling of buffer location at location 200, buffer parameter information may be entered for both the sample and the titrant.

Once the required information is provided using the "modify buffer parameters" sub-system 158, control is passed from buffer parameter menu 164 to the calling sub-system, such as data analysis sub-system 64, as illustrated by line 166.

Referring again to data analysis sub-system 64 as shown in FIG. 9, once the buffer parameters are initially set, a buffer template file can be made at location 210. Location 210 is connected to menu 154 by two-way line 212. All of the parameters with their current values are saved. Such a buffer template may be later read in at location 126 of sub-system 62, illustrated in FIG. 3. It is then possible to modify titrant and sample parameters at location 214 using two-way line 216, in the same fashion as at location 130 of sub-system 62, illustrated in FIG. 3.

A calibration segment file may be made using known experimental data and the model at location 218, as shown by two-way line 220. The calibration segment file is then used on a different file at location 102 of the import data sub-system 62, illustrated in FIG. 3, as discussed above.

pH data is typically curve-fitted with the model using a curve-fitting method at location 222, as shown by two-way line 224. The curve-fitting method employed is based in part on a non-linear least square fitting scheme as outlined by P. R. Bevington, *Data Reduction and Error Analysis for the Physical Sciences*, McGraw-Hill, New York, 1969, which is incorporated herein by reference.

The goal of the iteration method is to optimize the parameter values which will minimize the deviation between the experimental data and the model function describing the system. The measure of this deviation is defined through the chi-square function $$X^2 \equiv \sum_{i=1}^{n} \left\{ \frac{1}{\sigma_i^2} [y_i - y(x_i)]^2 \right\} \quad (48)$$

where the $\sigma_i$ are the uncertainties in the data points $y_i$ for the function $y(x)$. In contrast to the conventional approach where $y_i$ is purely from experiment and $y(x_i)$ is purely a theoretical function, the equation has been modified to become $$X^2 = \sum_{i=1}^{n} \{\delta v_i - \delta v(pH_i)\}^2 \quad (49)$$

where $\delta v_i$ is the normalized titrant volume from Equation (20), $\delta v$ is the modeled normalized titrant volume from Equation (34), and $pH_i$ is taken as the measured pH referenced to the same data point used in defining $\delta v_i$. The uncertainties have been given a unity value since there appears to be no significant advantage to weighting the data.

A preferred iteration method of $X^2$ is known as the gradient-expansion algorithm. The algorithm balances two search methods in a fashion which has the greatest possibility of rapid convergence. When the variable values are far from the optimum, a gradient search technique is used to increment the parameters in the direction of the greatest change towards a smaller value of the chi-square function.

Another preferred iteration method is related to a parabolic extrapolation of $X^2$ involving a Taylor's series expansion, which is effective when the variable values are close to optimum. The equation parameters are the unknown variables to be optimized. These parameters are selected from a list of $pK_a$s and concentrations of the buffers which are in the sample and titrant solutions.

The disclosed methods usually converges within a few iterations depending on the orthogonality of the parameters. The stringency of convergence criteria can be changed by the user to better match the level of experimental noise and the time available for analysis. To save computing time, in large data sets typically only every fourth or even eighth data point is used for curve fitting until an intermediate convergence criterion is reached. Then the remaining iterations use all of the data points. Concurrent with the iteration, intermediate fitting curves of the form $d\delta v/dpH$ and $\delta v = \delta v(pH)$ are typically plotted, like those shown in FIGS. 5 and 6 for acid titration of a very weak multi functional base, and FIGS. 7 and 8 for base titration of a mixture of weak acids. Such curves are typically displayed to give visual feedback as to the correctness of the choice of the buffer set. A poor choice occasionally leads to convergence to an erroneous "local minimum" solution. If this occurs, the visible discrepancies between the fitted and experimental curves, especially the derivative curve, usually make the necessary buffer-set corrections self-evident.

Upon convergence, options are available at location 226, by means of line 227, if desired, to analyze the resulting fitted curve for systematic errors (as opposed to random noise). Residual analysis and output is discussed above in greater detail with respect to location 198 of sub-system 158, illustrated in FIG. 10. Control is returned to Data Analysis Menu 154 by means of line 228. Main program menu 58 can be returned to at any time from menu 154, as shown by line 230.

Figure 13:
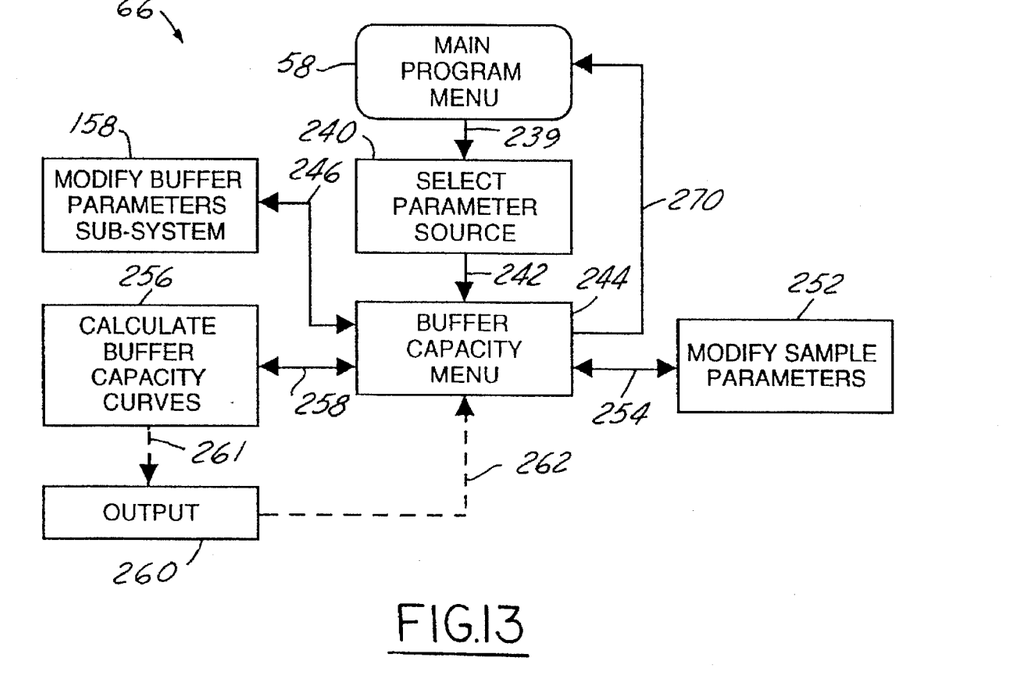
FIG. 13 is a more detailed schematic of a "buffer capacity sub-system," illustrated in FIG. 2.

Another capability of the system is the ability to generate a buffer capacity curve from a given buffer set as illustrated by a schematic of buffer capacity sub-system 66 in FIG. 13. Buffer capacity sub-system 66 is organized in a fashion very similar to that of data analysis sub-system 64. A parameter source is selected at location 240 which is tied to main program menu 58 by two-way line 239, and may include prior calculations, an inverted data file, or resident parameters. Then, as illustrated by line 242, a buffer capacity menu 244 is available. The modify buffer parameters sub-system 158 may be selected as illustrated by two-way line 246. Solvent parameters such as $pK_w$ and solvent concentration may be modified at location 252, as shown by two-way line 254. Buffer capacity curves may be calculated at location 256, connected to menu 244 by two-way line 258. The buffer capacity curves are calculated by using the equations derived from the model in the limiting case of an infinitesimal titrant addition, as discussed above. See, equations (45) and (46). Capacity curves and related output may be optionally generated at location 260, connected to location 256 by dashed line 261. Location 260 is connected to buffer capacity menu 244 by dashed line 262.

Figure 14:
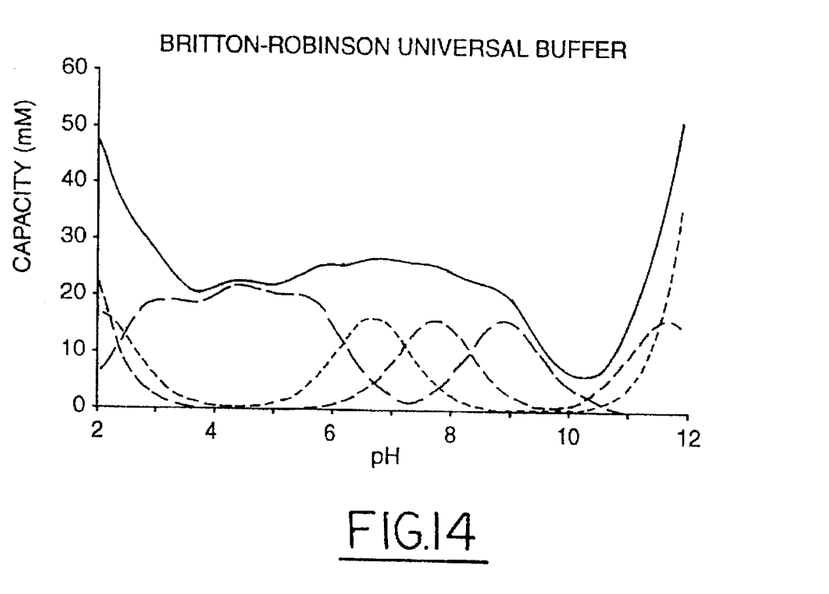
FIG. 14 is a plot of buffer capacity of a mixture and its deconvoluted components according to the present invention.

FIG. 14 illustrates the buffer capacity of a commonly used mixture of buffers, known as the Britton-Robinson universal buffer, as calculated from literature concentration and $pK_a$ data.

An example of the buffer capacity curve derived from titration data, for the system of FIGS. 4 through 6, is illustrated in FIG. 15. Curve 266 represents the total buffer capacity, while curves 268 and 270 represent the buffer capacity of citric acid and medium respectively. The Y-axis is the capacity in mM and the X-axis is the pH. The result is a "pH spectrum" of the sample, from which components can be identified by their $pK_a$'s. One advantage to plotting a buffer capacity curve derived from an actual titration is in comparing results of different titrations while eliminating the influence of titrant parameters and of sample dilution.

Once data is displayed and output optionally saved, buffer capacity menu 244 of FIG. 13 may be returned to as shown by dashed line 262. From menu 244, the main program menu 58 may be returned to as shown by line 270.

Figure 16:
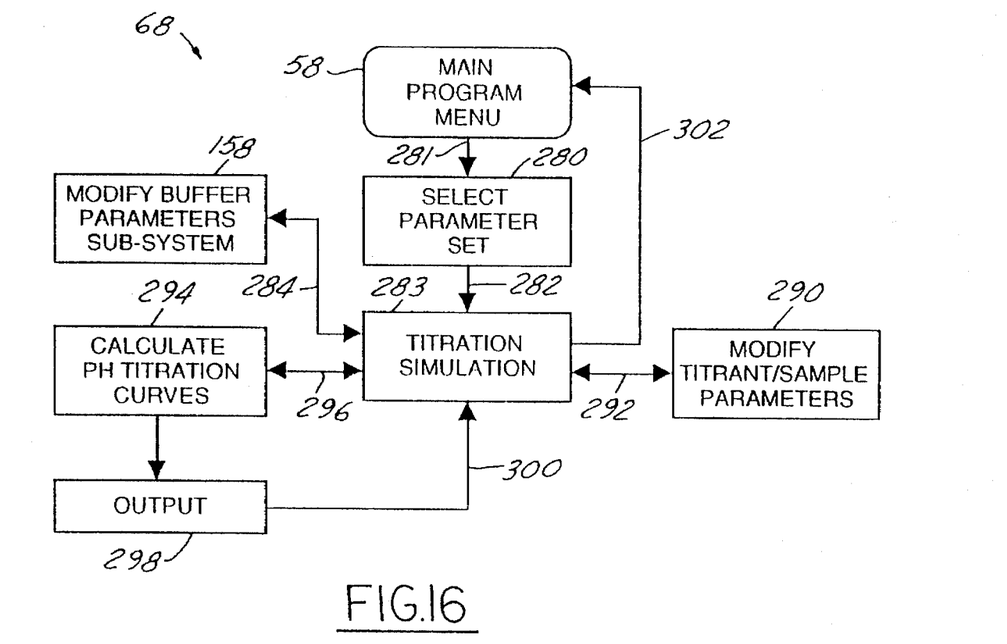
FIG. 16 is a more detailed schematic of a "titration simulator sub-system", illustrated in FIG. 2.

A titration simulator sub-system 68 is also available within system 30, as illustrated in the schematic of FIG. 16. The sub-system is very similar to that of the data-analysis sub-system. Parameters are selected at location 280, connected to main program menu 58 by line 281, and may be prior calculations, resident parameters, or an inverted data file. A line 282 connects location 280 with a titration simulation menu 283. Modify buffer parameters sub-system 158 may be accessed as shown by two-way line 284, and a buffer template file may be saved at location 286 as shown by two-way line 288. It is possible to modify the titrant and sample parameters at location 290, connected to menu 283 by two-way line 292. pH titration curves may be calculated at location 294, connected to menu 283 by two-way line 296. Unlike with data analysis sub-system 64, however, no curve fitting is required. Instead, the actual equations of the model are solved for $[H]_m$. The choice of equations will depend on the nature of the buffer parameters, as would be understood by one skilled in the art. For example, equation (21) can be used for the case displayed in FIG. 5 since there are no buffers in the titrant. For the more general case of buffers present in the titrant, equation (34) is used. Output may be generated at location 298, as shown by two-way line 300. The main program menu 58 may be accessed at any time from titration simulator menu 283, as shown by line 302.

Finally, the program of system 30 includes a help sub-system 60. Sub-system 60 is preferably keyed to current display screen commands and options.

The method of the present invention has been tested for several mixtures of buffers which cannot be determined by regular pH titration because of the proximity of their $pK_a$'s (0.4–1.5 pH units apart). Among the mixtures tested include: acetic and glycolic acids; acetic and tartaric acids; chloroacetic and glycolic acids; carbonate and borate; ammonia and methylamine; tartaric and malic acids (requires calibration curve); binary and ternary mixtures of 3- and 4-picoline and 2,6-lutidine. Most of these mixtures have at least one $pK_a$ outside of the 4–10 range. Still, even without applying a pH/concentration calibration procedure, the error in the total buffer concentration found by curve-fitting was typically one percent (1%) or less, and the error in the concentration of the individual components was typically not more than two to three percent (2–3%) of the total buffer concentration. Use of the "dynamic calibration" procedure further improves on these results.

The present invention may be used for the determination of relatively simple component mixtures with close $pK_a$'s, for which the methods of choice now used are chromatographic (e.g., HPLC, ion chromatography, or GC/MS). There are many such opportunities in analytical practice, e.g., in the food and beverage industries (e.g., tartaric and acetic acids in wine, tartaric and malic acid in grapes, various acids in soft beverages, amines in fish), and also in medical or veterinary analysis, chemical production, soil analysis, and the like. It is also envisioned that the present invention may be used in educating students to concepts such as pH and titration, acidity constants, buffers, and buffer capacity, particularly since it may provide a visual pH spectrum of information. The invention avoids oversimplifications that known systems have. Finally, the invention offers special capabilities for providing information about unknown substances. It can determine $pK_a$'s of new compounds, distinguish between single compounds and mixtures of structural isomers, spot reaction by-products, etc. In a quality control environment, when complex mixtures are analyzed, one can define a given product by assigning a set of constant, equally spaced $pK_a$'s for the pH range of interest and curve-fitting the titration curve. The resulting set of concentrations can define the mixture and serve as a numerical, easily tabulated "fingerprint" of the sample.

Preferred embodiments of the present invention have been disclosed. A person of ordinary skill in the art would realize, however, that certain modifications would come within the teachings of this invention. Therefore, the following claims should be studied to determine the true scope and content of the invention.

What is claimed is:

1. A method for modeling a pH titration to selectively determine the characteristics of sample and titrant components, comprising the steps of:

generating a series of data points relating volume of a titrant to pH of a mixture of a sample and said titrant;

postulating a number of buffers in at least one of said titrant and said sample, each of said buffers having one or more acidity constants;

determining an initial estimate of the number of said acidity constants and an estimated value for each of said acidity constants for each of said buffers; and applying a model that relates said volume of said titrant to hydrogen concentration in said mixture and is based on mass balance by requiring that molar amounts of hydrogen ion, hydroxide ion and said buffers in said sample and said titrant be conserved in said mixture wherein no volume additivity assumptions are made, said model further including said initial estimate of said number of said buffers and said initial estimate of said number of said acidity constants and said value for each of said acidity constants for each of said buffers.

2. A method as recited in claim 1, wherein said applying step comprises the sub-steps of plotting derivative curves of said titrant volume versus pH for said model and said data points, reviewing visually a resulting "goodness of fit" between said data points and said model, and curve-fitting said model to said data points using an iterative method.

3. A method as recited in claim 2, wherein said applying step comprises the further sub-step of superimposing a residual curve onto said derivative curves of the form $$\left[\frac{d\delta v}{dpH}\right]_{data} - \left[\frac{d\delta v}{dpH}\right]_{model}$$

where $\delta v$ reflects the normalized titrant volume.

4. A method as recited in claim 2, wherein said applying step comprises the further sub-step of deconvoluting said derivative curve of said model into separate contributions of the sample components.

5. A method as recited in claim 1, wherein said applying step comprises the step of solving an equation of the form:

$$\delta v = \frac{([H]_s + [HW]_s + \alpha_s)([W]_m + [HW]_m) - ([H]_m + [HW]_m)([W]_s + [HW]_s)}{([H]_m + [HW]_m)([W]_t + [HW]_t) - ([H]_t + [HW]_t + \beta_t)([W]_m + [HW]_m)}$$

where $\delta v$ is the modeled normalized titrant volume, subscripts s, t, and m refer to quantities in said sample, said titrant and said mixture, respectively, [H] is a molar concentration of free hydrogen, [W] is a molar concentration of hydroxide, [HW] is a concentration of a solvent in said mixture, and $\alpha_s$ is a function in the form of $$\alpha_s = [A_T]\left[\frac{\sum_{j=1}^{n_\alpha}\left(j[H]_s^j \prod_{i=1}^{j} k_i\right)}{1 + \sum_{j=1}^{n_\alpha}\left([H]_s^j \prod_{i=1}^{j} k_i\right)} - \frac{\sum_{j=1}^{n_\alpha}\left(j[H]_m^j \prod_{i=1}^{j} k_i\right)}{1 + \sum_{j=1}^{n_\alpha}\left([H]_m^j \prod_{i=1}^{j} k_i\right)}\right]$$

for a multiprotic buffer of degree $n_\alpha$ and where $\Pi^j_{i=1}$ denotes the product function and k is a dissociation constant, and $\beta_t$ is a function in the form of $$\beta_t = [A_T]_t\left[n_\beta - \frac{\sum_{j=1}^{n_\beta}\left(j[H]_m^j \prod_{i=1}^{j} k_i\right)}{1 + \sum_{j=1}^{n_\beta}\left([H]_m^j \prod_{i=1}^{j} k_i\right)}\right]$$

for a muliprotic buffer of degree $n_\beta$.

6. A method as recited in claim 5, wherein said applying step comprises the sub-step of curve-fitting said model to said data points using a chi-square function of the form $$X^2 = \sum_{i=1}^{n} \{\delta v_i - \delta v(pH_i)\}^2$$

where $\delta v_i$ is the normalized titrant volume and $pH_i$ is taken as the measured pH referenced to the same data points used in defining $\delta v_i$.

7. A method as recited in claim 1, wherein said selecting step comprises the sub-step of excluding said data points near a titration end point.

8. A method as recited in claim 1, said determining steps comprising the sub-steps of:
   inverting said data points to express said pH as a function of said volume of said titrant;
   plotting a derivative of said volume of said titrant versus said pH as a function of said pH; and
   locating a maxima from said plotting step to provide said initial estimate of unknown acidity constants.

9. A method as recited in claim 1, comprising the step of generating a buffer capacity curve by assuming that said titrant has infinite concentration and in said applying step.

10. A method as recited in claim 1, wherein said generating step comprises a sub-step of collecting experimental data, said collecting step comprising the further sub-step of modifying said experimental data by collecting calibration data under similar conditions to yield accurate hydrogen ion concentration data for use with said model.

11. A method for modeling a pH titration to selectively determine the characteristics of sample and titrant components, comprising the steps of:
   generating a series of data points relating volume of a titrant to pH of a mixture of a sample and said titrant;
   postulating a number of buffers in at least one of said titrant and said sample, each of said buffers having one or more acidity constants;
   determining an initial estimate of the number of said acidity constants and an estimated value for each of said acidity constants for each of said buffers, comprising the sub-steps of:
      inverting said data points to express said pH as a function of said volume of said titrant,
      plotting a derivative of said volume of said titrant versus said pH as a function of said pH, and
      locating a maxima from said plotting step to provide said initial estimate of unknown acidity constants; and
   applying a model that relates said volume of said titrant to hydrogen concentration in said mixture and is based on mass balance by requiring that molar amounts of hydrogen ion, hydroxide ion and said buffers in said sample and said titrant be conserved in said mixture wherein no volume additivity assumptions are made, said model further including said initial estimate of said number of said buffers and said initial estimate of said number of said acidity constants and said value for each of said acidity constants for each of said buffers.

12. A method as recited in claim 11, wherein said applying step comprises the sub-steps of plotting derivative curves of said titrant volume versus pH for said model and said data points, reviewing visually a resulting "goodness of fit" between said data points and said model, and curve-fitting said model to said data points using an iterative method.

13. A method as recited in claim 11, wherein said applying step comprises the step of solving an equation of the form:

$$\delta v = \frac{([H]_s + [HW]_s + \alpha_s)([W]_m + [HW]_m) - ([H]_m + [HW]_m)([W]_s + [HW]_s)}{([H]_m + [HW]_m)([W]_t + [HW]_t) - ([H]_t + [HW]_t + \beta_t)([W]_m + [HW]_m)}$$

where $\delta v$ is the modeled normalized titrant volume, subscripts s, t, and m refer to quantities in said sample, said titrant and said mixture, respectively, [H] is a molar concentration of free hydrogen, [W] is a molar concentration of hydroxide, [HW] is a concentration of a solvent in said mixture, and $\alpha_s$ is a function in the form of $$\alpha_s = [A_T]\left[\frac{\sum_{j=1}^{n_\alpha}\left(j[H]_s^j\prod_{i=1}^{j}k_i\right)}{1+\sum_{j=1}^{n_\alpha}\left([H]_s^j\prod_{i=1}^{j}k_i\right)} - \frac{\sum_{j=1}^{n_\alpha}\left(j[H]_m^j\prod_{i=1}^{j}k_i\right)}{1+\sum_{j=1}^{n_\alpha}\left([H]_m^j\prod_{i=1}^{j}k_i\right)}\right]$$

for a multiprotic buffer of degree $n_\alpha$ and where $\Pi_{i=1}^j$ denotes the product function and k is a dissociation constant, and $\beta_t$ is a function in the form of $$\beta_t = [A_T]_t\left[n_\beta - \frac{\sum_{j=1}^{n_\beta}\left(j[H]_m^j\prod_{i=1}^{j}k_i\right)}{1+\sum_{j=1}^{n_\beta}\left([H]_m^j\prod_{i=1}^{j}k_i\right)}\right]$$

for a muliprotic buffer of degree $n_\beta$.

14. A method as recited in claim 13, wherein said applying step comprises the sub-step of curve-fitting said model to said data points using a chi-square function of the form $$X^2 = \sum_{i=1}^{n}\{\delta v_i - \delta v(pH_i)\}^2$$

where $\delta v_i$ is the normalized titrant volume and $pH_i$ is taken as the measured pH referenced to the same data points used in defining $\delta v_i$.

15. A method as recited in claim 11, wherein said generating step comprises the sub-steps of:
   delivering drops of said titrant to said sample at a known preselected rate;
   measuring pH of said mixture as each of said drops of said titrant are added to said sample; and
   recording said pH versus said volume of said titrant.

16. A method as recited in claim 15, wherein said measuring step comprises an electrode connected to a computer, said computer performing said recording step by means of a connection with an automatic titrator performing said delivering step.

17. A method for modeling a pH titration to selectively determine the characteristics of sample and titrant components, comprising the steps of:
   generating a series of data points relating volume of a titrant to pH of a mixture of a sample and said titrant, said generating step including the sub-steps of:
      delivering drops of said titrant to said sample at a known preselected rate using an automatic titrator;
      measuring pH of said mixture as each of said drops of said titrant are added to said sample using a sensor, and
      recording said pH versus an addition to said mixture of each of said drops of said titrant, a computer connected to said automatic titrator and said sensor;
   postulating a number of buffers in at least one of said titrant and said sample, each of said buffers having a number of acidity constants;
   determining an initial estimate of said number of said acidity constants and an estimated value for each of said acidity constants for each of said buffers;
   locating a maxima from said generating step to provide said initial estimate of unknown acidity constants; and applying a model that relates said volume of said titrant to hydrogen concentration in said mixture and is based on mass balance by requiring that molar amounts of hydrogen ion, hydroxide ion and said buffers in said sample and said titrant be conserved in said mixture, said model further including said initial estimate of said number of said buffers and said initial estimate of said number of said acidity constants and said value for each of said acidity constants for each of said buffers.

18. A method as recited in claim 17, wherein said applying step comprises the sub-steps of:

plotting derivative curves of said titrant volume versus pH for said model and said data points;

reviewing visually a resulting "goodness of fit" between said data points and said model, and curve-fitting said model to said data points using an iterative method; and solving an equation of the form:

$$\delta v = \frac{([H]_s + [HW]_s + \alpha_s)([W]_m + [HW]_m) - \frac{([H]_m + [HW]_m)([W]_s + [HW]_s)}{([H]_m + [HW]_m)([W']_t + [HW]_t) - ([H']_t + [HW]_t + \beta_t)([W]_m + [HW]_m)}}$$

where $\delta v$ is the modeled normalized titrant volume, subscripts s, t, and m refer to quantities in said sample, said titrant and said mixture, respectively, [H] is a molar concentration of free hydrogen, [W] is a molar concentration of hydroxide, [HW] is a concentration of a solvent in said mixture, and $\alpha_s$ is a function in the form of $$\alpha_s = [A_T] \left[ \frac{\sum_{j=1}^{n_\alpha} \left( j[H]^j \prod_{i=1}^{j} k_i \right)}{1 + \sum_{j=1}^{n_\alpha} \left( [H]^j \prod_{i=1}^{j} k_i \right)} - \frac{\sum_{j=1}^{n_\alpha} \left( j[H]_m^j \prod_{i=1}^{j} k_i \right)}{1 + \sum_{j=1}^{n_\alpha} \left( [H]_m^j \prod_{i=1}^{j} k_i \right)} \right]$$

for a multiprotic buffer of degree $n_\alpha$ and where $\Pi_{i=1}^{j}$ denotes the product function and k is a dissociation constant, and $\beta_t$ is a function in the form of $$\beta_t = [A_T]_t \left[ n_\beta - \frac{\sum_{j=1}^{n_\beta} \left( j[H]_m^j \prod_{i=1}^{j} k_i \right)}{1 + \sum_{j=1}^{n_\beta} \left( [H]_m^j \prod_{i=1}^{j} k_i \right)} \right]$$

for a muliprotic buffer of degree $n_\beta$.

19. A method as recited in claim 18, wherein said determining step comprises the sub-steps of:

inverting said data points to express said pH as a function of said volume of said titrant;

plotting a derivative of said volume of said titrant versus said pH as a function of said pH; and Locating a maxima from said plotting step to provide said initial estimate of unknown acidity constants.

* * * * *